(12) United States Patent
Gulani et al.

(10) Patent No.: US 10,379,189 B2
(45) Date of Patent: Aug. 13, 2019

(54) SIMULTANEOUS MAGNETIC RESONANCE ANGIOGRAPHY AND PERFUSION WITH NUCLEAR MAGNETIC RESONANCE FINGERPRINTING

(71) Applicant: Case Western Reserve University, Cleveland, OH (US)

(72) Inventors: Vikas Gulani, Cleveland Heights, OH (US); Mark Griswold, Shaker Heights, OH (US); Dan Ma, Cleveland Heights, OH (US); Katherine Wright, Macedonia, OH (US); Nicole Seiberlich, Cleveland Heights, OH (US)

(73) Assignee: Case Western Reserve University, Cleveland, OH (US)

( * ) Notice: Subject to any disclaimer, the term of this patent is extended or adjusted under 35 U.S.C. 154(b) by 584 days.

(21) Appl. No.: 14/444,737

(22) Filed: Jul. 28, 2014

(65) Prior Publication Data
US 2016/0025835 A1  Jan. 28, 2016

(51) Int. Cl.
*A61B 5/00* (2006.01)
*G01R 33/563* (2006.01)
(Continued)

(52) U.S. Cl.
CPC ........ *G01R 33/5635* (2013.01); *A61B 5/0035* (2013.01); *A61B 5/055* (2013.01);
(Continued)

(58) Field of Classification Search
None
See application file for complete search history.

(56) References Cited

U.S. PATENT DOCUMENTS

2002/0010397 A1* 1/2002 Prince .................... A61B 5/411
600/420
2012/0235678 A1* 9/2012 Seiberlich ............ G01R 33/543
324/307

OTHER PUBLICATIONS

Simultaneous Magnetic Resonance Angiography and Perfusion (MRAP) Measurement: Initial Application in Lower Extremity Skeletal Muscle by Wright et al.; pub. online on Feb. 6, 2013. at http://onlinelibrary.wiley.com/doi/10.1002/jmri.24020/abstract.*

(Continued)

*Primary Examiner* — Katherine L Fernandez
*Assistant Examiner* — Michael S Kellogg
(74) *Attorney, Agent, or Firm* — Quarles & Brady LLP; Jack Cook (57) ABSTRACT

Embodiments associated with combined magnetic resonance angiography and perfusion (MRAP) and nuclear magnetic resonance (NMR) fingerprinting are described. One example apparatus repetitively and variably samples a (k, t, E) space associated with an object to acquire a set of NMR signals that are associated with different points in the (k, t, E) space. Sampling is performed with t and/or E varying in a non-constant way. The apparatus includes a signal logic that produces an NMR signal evolution from the NMR signals and a characterization logic that characterizes a resonant species in the object as a result of comparing acquired signals to reference signals. The apparatus includes an MRAP logic that simultaneously performs MR angiography and produces quantitative perfusion maps. A multi-factor MR bio-imaging panel is produced from a combination of the data provided by the MRAP and NMR fingerprinting. Diagnoses may be made from the multi-factor MR bio-imaging panel.

15 Claims, 9 Drawing Sheets

(51) Int. Cl.
  *A61B 5/055* (2006.01)
  *G01R 33/44* (2006.01)
(52) U.S. Cl.
  CPC ...... *G01R 33/56366* (2013.01); *A61B 5/4064* (2013.01); *G01R 33/448* (2013.01)

(56) References Cited

OTHER PUBLICATIONS

Accuracy of Semiautomated Analysis of 3D Contrast-Enhanced Magnetic Resonance Angiography for Detection and Quantification of Aortoiliac Stenoses by de Vries et al.; pub. Investigative Radiology • vol. 40, No. 8, Aug. 2005 pp. 495-503.*

* cited by examiner

SIMULTANEOUS MAGNETIC RESONANCE ANGIOGRAPHY AND PERFUSION WITH NUCLEAR MAGNETIC RESONANCE FINGERPRINTING

FEDERAL FUNDING NOTICE

This invention was made with government support under the grant(s) RO1HL094557, 1KL2RR024990, 1K99EB011527, and T32EB007509 awarded by the National Institutes of Health. The government has certain rights in the invention.

BACKGROUND

The pathology in peripheral arterial disease (PAD) may be multifactorial, including both a perfusion deficit and metabolic/structural changes in the skeletal muscle. Yet conventional approaches to analyzing PAD may have analyzed single factors at a time. Diagnosing PAD, tracking the progression of PAD, tracking the efficacy of a treatment for PAD, or other perfusion related analysis have been limited by single factor approaches. When performing a liver or kidney transplant, understanding the location, health, function, and other information about vasculature associated with the organ may be essential to a successful procedure. Conventional imaging approaches to understanding pre-surgical arterial information may also have been analyzed using a single factor at a time. When performing a resection of a tumor in, for example, a kidney or liver, understanding the location, health, function, and other information about how the tumor is vascularized may be important to a successful procedure. Yet once again, conventional imaging approaches may have analyzed a single factor at a time. Similarly, when preparing for brain surgery (e.g., implanting deep brain stimulation electrode, resecting tumor), understanding the location, health, function, and other information about how the relevant region is vascularized may be important to a successful procedure.

Vascular pathologies can affect large and small vessels, and can manifest as perfusion deficits from downstream effects of large vessel disease or directly from small vessel disease. Comprehensive vascular evaluation may be improved by assessing both large and small vessels. Magnetic resonance angiography (MRA) has been used to image large arteries to, for example, assess arterial pathology. While MRA is useful for large vessels, MRA is less useful for the microvasculature. Therefore, dynamic contrast-enhanced (DCE) techniques for acquiring quantitative perfusion maps have been applied to analyze the microvasculature. Conventional approaches may have performed a pharmacokinetic analysis of an administered contrast agent (e.g., Gadolinium). Conventionally, magnetic resonance imaging (MRI) based DCE perfusion and MRA have been be used to separately assess the macro- and microvasculature. Since MRA and perfusion exams have conventionally used a separate, full-dose (as calculated by patient weight) contrast bolus, the two studies have conventionally been performed on different days to avoid contamination of the second exam and contrast double-dosing. These factors have effectively precluded the use of MRI to evaluate both micro-vascular and macro-vascular components of disease simultaneously. Thus, the multifactorial etiologies of vascular pathologies such as PAD may have been incompletely explored.

Time-resolved MRA (trMRA) techniques have been performed by acquiring three dimensional (3D) images at several points in time to dynamically visualize arterial anatomy at different phases of contrast agent arrival. These images may have contained high spatial resolution data concerning large vessels. The data on the large vessels may have included some embedded tissue enhancement information. However, trMRA image acquisitions are optimized for visualizing vascular anatomy and not DCE analysis. Thus, MRA and Perfusion (MRAP) provided a simultaneous approach that maintained the high spatial resolution needed to visualize the vasculature while also achieving high temporal resolution and sufficient tissue signal-to-noise ratio (SNR) to accurately capture changes in contrast agent concentration used in estimating perfusion. By simultaneously acquiring angiography images and calculating quantitative perfusion parameters, MRAP accomplished both small and large vessel assessment in a single exam and contrast dose. However, in conventional MRAP, MRI relaxation parameters (e.g., T1, T2) may only have been available as crude baseline measures. Conventional MRAP is described in *Simultaneous Magnetic Resonance Angiography And Perfusion (MRAP) Measurement: Initial Application in Lower Extremity Skeletal Muscle*, Wright et al., JOURNAL OF MAGNETIC RESONANCE IMAGING 38:1237-1244 (2013), which is incorporated herein in its entirety.

Conventional magnetic resonance (MR) pulse sequences included a preparation phase, a waiting phase, and an acquisition phase that serially produced signals from which images could be made serially. The preparation phase determined when a signal could be acquired and determined the properties of the acquired signal. For example, a first pulse sequence may have been designed to produce a T1-weighted signal at a first echo time (TE) while a second pulse sequence may have been designed to produce a T2-weighted signal at a second TE. These conventional pulse sequences were typically designed to provide qualitative results where data were acquired with various weightings or contrasts that highlighted a particular parameter (e.g., T1 relaxation, T2 relaxation).

When MR images were generated, they may have been viewed by a radiologist and/or surgeon who interpreted the qualitative images for specific disease signatures. The radiologist may have examined multiple image types (e.g., T1-weighted, T2-weighted) acquired in multiple imaging planes to make a diagnosis. The radiologist or other individual examining the qualitative images may have needed particular skill to be able to assess changes from session to session, from machine to machine, and from machine configuration to machine configuration. Thus, the qualitative images were only as good as the image interpreter and all image based (e.g., qualitative) diagnoses ended up being subjective.

Magnetic resonance fingerprinting (MRF) employed a series of varied sequence blocks that simultaneously produced different signal evolutions in different resonant species (e.g., tissues) to which the radio frequency (RF) in an MR pulse sequence was applied. The term "resonant species", as used herein, refers to an item (e.g., water, fat, tissue, material) that can be made to resonate using nuclear magnetic resonance (NMR). By way of illustration, when example apparatus and methods apply RF energy to a volume that has both bone and muscle tissue, then both the bone and muscle tissue will produce an NMR signal. However the "bone signal" and the "muscle signal" will be different. The different signals can be collected over a period of time to identify a signal evolution for the volume. Resonant species in the volume can then be characterized by comparing the signal evolution to known evolutions.

Conventional MRF may access a large set of known evolutions in a dictionary. Characterizing the resonant species can include identifying different properties of a resonant species (e.g., T1, T2, diffusion resonant frequency, diffusion co-efficient, spin density, proton density). Additionally, other properties including, but not limited to, tissue types, materials, and super-position of attributes (e.g., T1, T2) can be identified.

MRF is described in United States Patent Application "Nuclear Magnetic Resonance (NMR) Fingerprinting", application Ser. No. 13/051,044, and in Magnetic Resonance Fingerprinting, Ma et al., Nature 495, 187-192 (14 Mar. 2013), the contents of both of which are incorporated herein by reference.

BRIEF DESCRIPTION OF THE DRAWINGS

The accompanying drawings, which are incorporated in and constitute a part of the specification, illustrate various example systems, methods, and other example embodiments of various aspects of the invention. It will be appreciated that the illustrated element boundaries (e.g., boxes, groups of boxes, or other shapes) in the figures represent one example of the boundaries. One of ordinary skill in the art will appreciate that in some examples one element may be designed as multiple elements or that multiple elements may be designed as one element. In some examples, an element shown as an internal component of another element may be implemented as an external component and vice versa. Furthermore, elements may not be drawn to scale.

DETAILED DESCRIPTION

Example apparatus and methods use simultaneous magnetic resonance angiography with perfusion (MRAP) to acquire a quantitative perfusion measurement and an angiogram image. Example apparatus and methods also simultaneously use magnetic resonance fingerprinting (MRF) to acquire quantitative data about relaxation parameters (e.g., T1, T2, M0). An MR imaging bio-marker panel is constructed from at least the angiogram image, the quantitative perfusion measurement, and the quantitative relaxation parameters. The combined panel provides more accurate information than single factor approaches. For example, perfusion in a tissue may be quantified simultaneously with the generation of images of the vasculature involved in perfusing the tissue. The image and quantitative data may facilitate making a diagnosis of disease, tracking disease severity, assessing the efficacy of a treatment, or other actions. The angiogram, quantitative perfusion data, and relaxation parameter data may be acquired in a single acquisition following a single administration of a contrast agent (e.g., gadolinium). The data may facilitate measuring regional alterations in perfusion, changes due to intervention or treatment, or other results.

MRAP facilitates simultaneously acquiring angiography images and calculating a quantitative perfusion parameter for a volume in a body. Magnetic resonance imaging (MRI) is an important clinical imaging tool used to investigate tissue structure, function, and pathology in a variety of organ systems. Individually, both tools provide useful information. Combining data acquired simultaneously using both approaches into a multi-factor MR bio-imaging panel improves over conventional approaches that use one technique or the other, or that use the techniques serially in two separate acquisitions following two separate contrast agent administrations.

In MRI, tissue types respond to the applied magnetic fields according to their intrinsic MR parameters (e.g., T1, T2, proton density M0), which are related to the tissue structure and microenvironment. Tissue structures and lesions are typically identified based on their relative hyper- or hypo-intense appearance in these variously weighted images. MRF offered the ability to simultaneously query T1, T2, and M0 from a single pseudo-randomized acquisition followed by pattern matching of the measured data to a simulated dictionary. Example apparatus and methods combine MRAP with MRF to facilitate identifying attributes associated with the vasculature (e.g., arterial flow) using the T1, T2, and M0 values derived from MRF and the angiogram and quantitative perfusion measures provided by MRAP. The quantitative perfusion measure may be, for example, $K^{trans}$, which is a function of perfusion (F), density (p), and hematocrit (Hct) (e.g., $K^{trans}=F\ \rho\ (1-Hct)$). In one example, p may be assumed to be 1.05 kg/L and Hct may be assumed to be 0.4.

MRF simultaneously provides quantitative values for multiple MR parameters. The quantitative mapping uses different combinations of MR parameters of interest, (e.g., T1, T2, off-resonance). Observed signal evolutions are matched to dictionary entries using, for example, template matching. In one example, the inner product is computed between a noisy signal and entries in a dictionary to find the stored signal evolution to which an acquired signal evolution matches. Parameter combinations unique to the dictionary entry that matched the acquired noisy signal may then be retrieved and provided.

MRF efficiently produces quantitative images of tissue parameters using pattern recognition between a dictionary and signals produced in response to the variable excitation schemes associated with MRF. The dictionary may be formed using the Bloch equations to simulate signal evolutions using different combinations of T1 relaxation times, T2 relaxation times, off-resonance frequencies, or other factors. In NMR, MRI, or ESR (electron spin resonance), a Bloch equation is a member of a set of macroscopic equations that are used to calculate the nuclear magnetization $M=(M_x, M_y, M_z)$ as a function of time when relaxation times T1 and T2 are present. These phenomenological equations were introduced by Felix Bloch and may also be referred to as the equations of motion of nuclear magnetization. In one embodiment Ri($\alpha$), $R_{RFij}(\alpha, \Phi)$, and R(G) may be viewed as Bloch equations.

Using pattern matching to compare acquired signal evolutions to known signal evolutions may include analyzing a cross-correlation between signal evolutions of different tissues acquired using sequence blocks having different parameters. Ideally, a signal evolution would fit to exactly one member of the multi-dimensional set of known evolutions. However, a signal evolution may have relationships with more than one reference signal. Thus, in one embodiment, comparing a signal evolution to a reference signal may result in an identification of a reference signal with which the signal evolution is related and a measurement characterizing the relationship. For example, a signal evolution may be identified as matching a reference signal to within a desired tolerance. Similarly, a signal evolution may be identified as being x % likely to match a reference signal. In another embodiment, a signal evolution may be identified as being a weighted sum of a number of reference signals. One dimension of the multi-dimensional set could, for example, be associated with a first set of acquisition and/or excitation parameters while a second dimension of the multi-dimensional set could, for example, be associated with a second set of excitation and/or acquisition parameters.

The following includes definitions of selected terms employed herein. The definitions include various examples and/or forms of components that fall within the scope of a term and that may be used for implementation. The examples are not intended to be limiting. Both singular and plural forms of terms may be within the definitions.

References to "one embodiment", "an embodiment", "one example", "an example", and so on, indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

"Computer-readable storage medium", as used herein, refers to a non-transitory medium that stores signals, instructions and/or data. A computer-readable medium may take forms, including, but not limited to, non-volatile media, and volatile media. Non-volatile media may include, for example, optical disks, magnetic disks, and so on. Volatile media may include, for example, semiconductor memories, dynamic memory, and so on. Common forms of a computer-readable medium may include, but are not limited to, a floppy disk, a flexible disk, a hard disk, a magnetic tape, other magnetic medium, an ASIC, a CD, other optical medium, a RAM, a ROM, a memory chip or card, a memory stick, and other media from which a computer, a processor or other electronic device can read.

"Logic", as used herein, includes but is not limited to hardware, firmware, software in execution on a machine, and/or combinations of each to perform a function(s) or an action(s), and/or to cause a function or action from another logic, method, and/or system. Logic may include a software controlled microprocessor, a discrete logic (e.g., ASIC), an analog circuit, a digital circuit, a programmed logic device, a memory device containing instructions, and so on. Logic may include one or more gates, combinations of gates, or other circuit components. Where multiple logical logics are described, it may be possible to incorporate the multiple logical logics into one physical logic. Similarly, where a single logical logic is described, it may be possible to distribute that single logical logic between multiple physical logics.

An "operable connection", or a connection by which entities are "operably connected", is one in which signals, physical communications, and/or logical communications may be sent and/or received. An operable connection may include a physical interface, an electrical interface, and/or a data interface. An operable connection may include differing combinations of interfaces and/or connections sufficient to allow operable control. For example, two entities can be operably connected to communicate signals to each other directly or through one or more intermediate entities (e.g., processor, operating system, logic, software). Logical and/or physical communication channels can be used to create an operable connection.

"User", as used herein, includes but is not limited to one or more persons, software, computers or other devices, or combinations of these.

Figure 1:
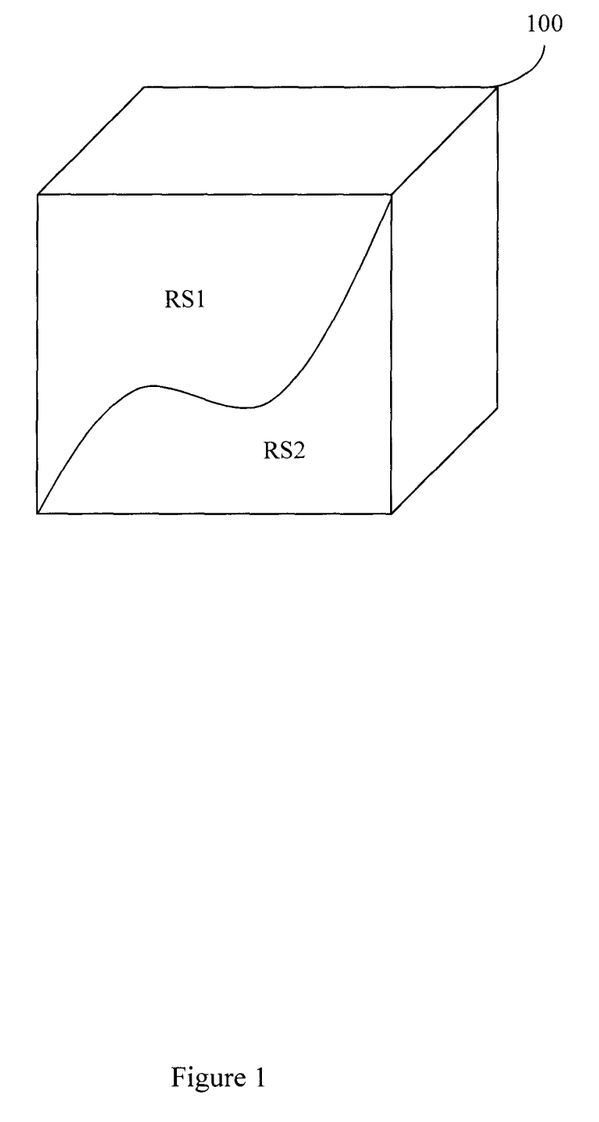
FIG. 1 illustrates a volume that contains two resonant species.

A brief review of MRF is provided herein with respect to FIGS. 1 through 3 and 9. FIG. 1 illustrates a volume 100 (e.g., voxel) that contains two resonant species RS1 and RS2. RS1 and RS2 may have different properties (e.g., relaxation parameters, non-relaxation parameters). For example, $T1_{RS1}$ may be less than $T1_{RS2}$ while $T2_{RS1}$ may be greater than $T2_{RS2}$. In another example, a spin density for RS1 may differ from a spin density for RS2. Conventional MR systems may acquire a T1 weighted data set in a first acquisition and then acquire a T2 weighted data set in a second acquisition and then register the data sets. MRF systems apply RF energy in a series of varied sequence blocks that cause volume 100 to simultaneously produce different NMR signals from both RS1 and RS2. A signal evolution can be produced from these simultaneously produced different NMR signals. Information including relaxation parameters (e.g., T1, T2), and non-relaxation parameters (e.g., diffusion coefficient, spin density, proton density, magnetic field strength) can be determined from the signal evolution by comparing the acquired signal to reference information. In one embodiment, the comparing may include pattern matching to other signal evolutions for which relaxation parameters are known. The resonant species RS1 and RS2 can then be characterized. Since different tissues have different known properties (e.g., relaxation parameters, non-relaxation parameters), different tissues can be identified using the characterization. While two resonant species are illustrated, a volume may include a greater or lesser number of resonant species.

Figure 2:
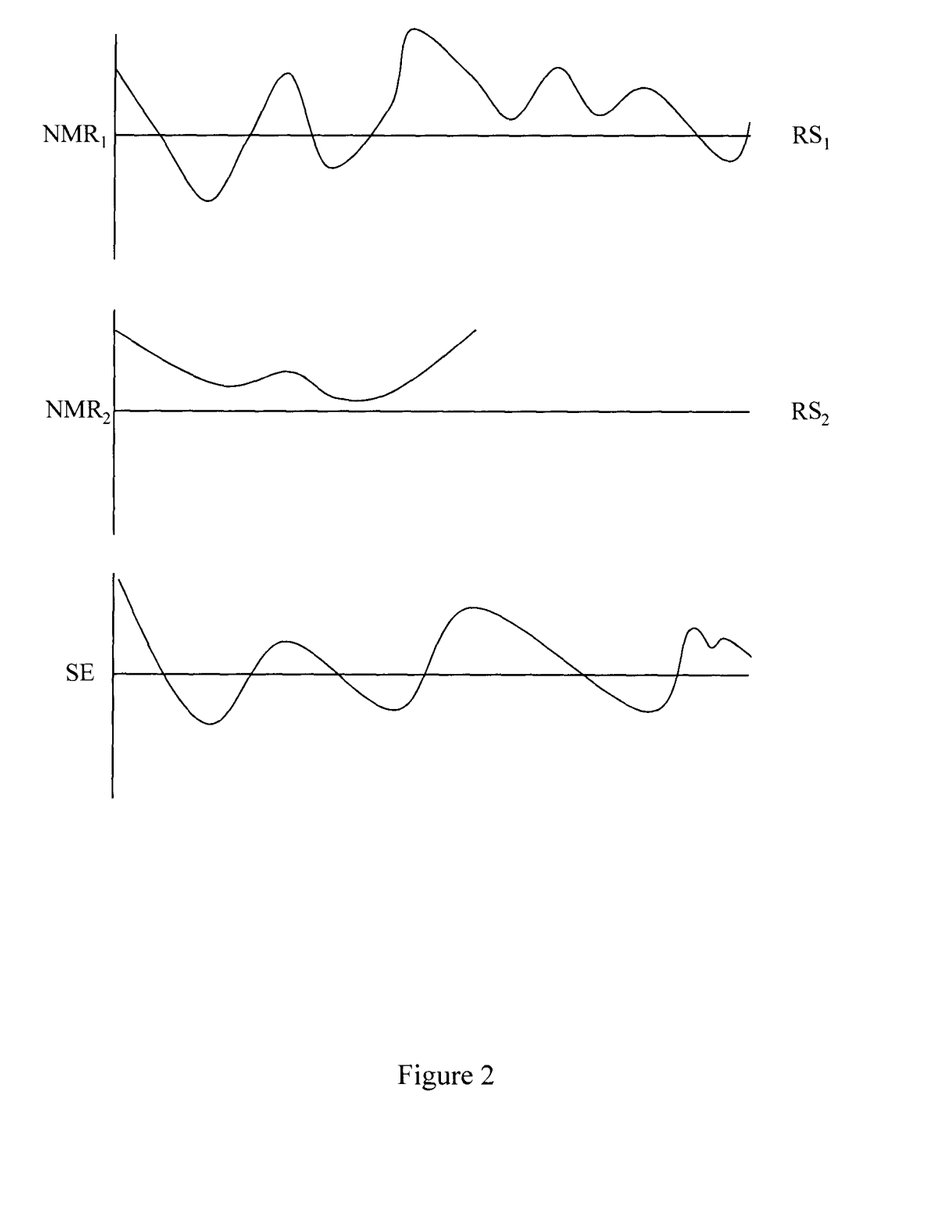
FIG. 2 illustrates two individual NMR signals received from two resonant species and a signal evolution derived from the two individual NMR signals.

FIG. 2 illustrates plots of two individual NMR signals $NMR_1$ and $NMR_2$ received from the two resonant species RS1 and RS2 in volume 100. $NMR_1$ includes data points generated by RS1 under different conditions at different times. $NMR_2$ includes data points generated by RS2 under the different conditions at the different times. Signal evolution SE results from $NMR_1$ and $NMR_2$ being generated and acquired simultaneously. The space from which the data points for $NMR_1$ and $NMR_2$ is acquired may be referred to as a (k, t, E) space, where in different examples, E refers to (T1, T2, D), (T1, T2, D, . . . ), (T1, T2, . . . ) where D refers to diffusion relaxation. In one example, both t and E may be non-linear. In another example, both t and E may be pseudo-random. Once again, while two plots associated with two resonant species are illustrated, a volume may include a greater or lesser number of resonant species and thus may produce a greater or lesser number of signals.

Figure 3:
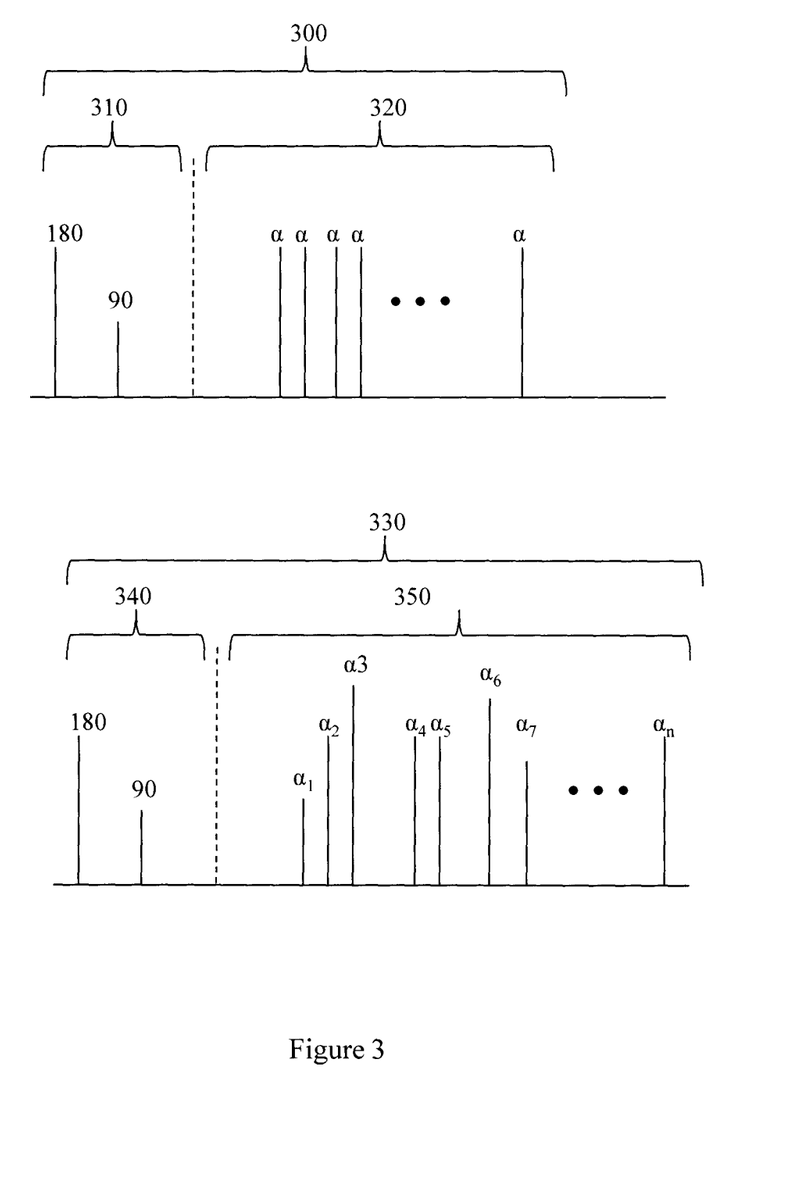
FIG. 3 compares and contrasts conventional sequence blocks to example sequence blocks.

FIG. 3 compares and contrasts conventional MR sequence blocks to MRF sequence blocks. Sequence block 300 includes a preparation phase 310 and an acquisition phase 320. During acquisition phase 320, multiple acquisitions using the same flip angle and the same interval between acquisitions may be performed. Sequence block 330 also includes a phase 340 and an acquisition phase 350. Notice that acquisition phase 350 is much longer than acquisition phase 320. Unlike acquisition phase 320 where parameters are either fixed or vary linearly, in acquisition phase 350 the parameters may vary widely, either non-linearly, randomly, and/or pseudo-randomly. Parameters that may vary include, but are not limited to, echo time, flip angle, phase encoding, and others. Note also that while phase 340 may, in some examples, be a preparation phase or preparation-like phase, phase 340 does not necessarily perform a conventional preparation.

Figure 9:
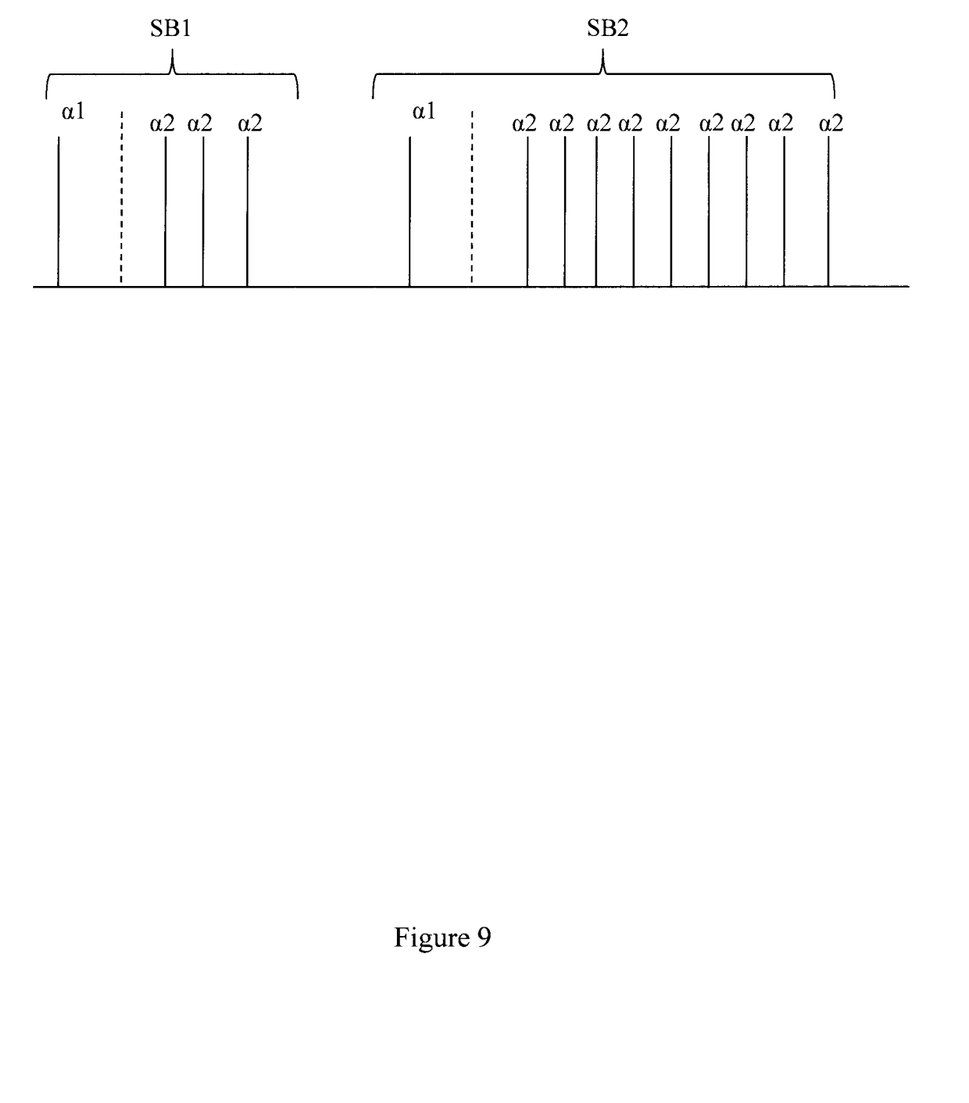
FIG. 9 illustrates an example set of sequence blocks.

FIG. 9 illustrates another example set of sequence blocks. A first sequence block SB1 has a first alpha pulse α1 and a series of identical α2 pulses. A second sequence block SB2 has the same first alpha pulse α1 and a different series of identical α2 pulses. The phase may be the same for the α2 pulses. Thus, in this example, the only difference between members of the set of sequence blocks is the number of α2 pulses.

Some portions of the detailed descriptions that follow are presented in terms of algorithms and symbolic representations of operations on data bits within a memory. These algorithmic descriptions and representations are used by those skilled in the art to convey the substance of their work to others. An algorithm, here and generally, is conceived to be a sequence of operations that produce a result. The operations may include physical manipulations of physical quantities. Usually, though not necessarily, the physical quantities take the form of electrical or magnetic signals capable of being stored, transferred, combined, compared, and otherwise manipulated in a logic, and so on. The physical manipulations create a concrete, tangible, useful, real-world result.

It has proven convenient at times, principally for reasons of common usage, to refer to these signals as bits, values, elements, symbols, characters, terms, numbers, and so on. It should be borne in mind, however, that these and similar terms are to be associated with the appropriate physical quantities and are merely convenient labels applied to these quantities. Unless specifically stated otherwise, it is appreciated that throughout the description, terms including processing, computing, determining, and so on, refer to actions and processes of a computer system, logic, processor, or similar electronic device that manipulates and transforms data represented as physical (electronic) quantities.

Example methods may be better appreciated with reference to flow diagrams. While for purposes of simplicity of explanation, the illustrated methodologies are shown and described as a series of blocks, it is to be appreciated that the methodologies are not limited by the order of the blocks, as some blocks can occur in different orders and/or concurrently with other blocks from that shown and described. Moreover, less than all the illustrated blocks may be required to implement an example methodology. Blocks may be combined or separated into multiple components. Furthermore, additional and/or alternative methodologies can employ additional, not illustrated blocks.

Figure 4:
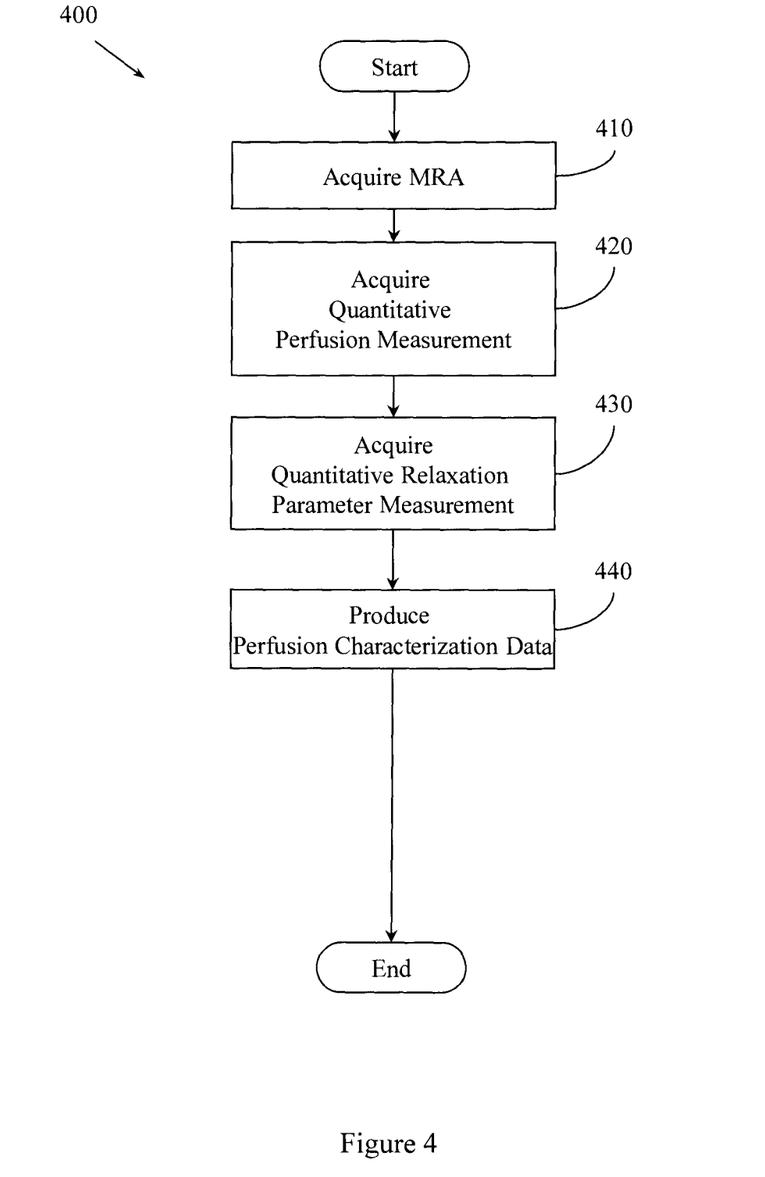
FIG. 4 illustrates an example method associated with simultaneous magnetic resonance angiography and perfusion (MRAP) with nuclear magnetic resonance fingerprinting (MRF).

FIG. 4 illustrates a method 400 associated with simultaneous magnetic resonance angiography and perfusion (MRAP) with nuclear magnetic resonance fingerprinting (MRF). Method 400 includes, at 410, controlling a magnetic resonance (MR) apparatus to acquire an MR angiograph (MRA) image associated with a volume in a body. In one embodiment, controlling the MR apparatus to acquire the MRA image includes controlling the MR apparatus to acquire two or more three dimensional images at two or more different points in time.

Method 400 also includes, at 420, controlling the MR apparatus to acquire a quantitative perfusion measurement associated with the volume. In one embodiment, controlling the MR apparatus to acquire the quantitative perfusion measurement includes controlling the MR apparatus to analyze spatial resolution data in the data associated with the two or more three dimensional images. The spatial resolution data may be included in the same data that is used to produce the MRA. The quantitative perfusion measure may be, for example, $K^{trans}$, which is a function of perfusion (F), density (ρ), and hematocrit (Hct) (e.g., $K^{trans}$=F ρ (1-Hct)). In one example, ρ may be assumed to be 1.05 kg/L and Hct may be assumed to be 0.4. While $K^{trans}$ is described, other quantitative perfusion measures may be employed.

Method 400 also includes, at 430, controlling the MR apparatus to acquire a quantitative relaxation parameter measurement associated with the volume by performing MRF on the volume. The quantitative relaxation parameter measurement may measure, for example, T1, T2, or other relaxation properties.

Method 400 also includes, at 440, producing a perfusion characterization data for the volume. In one embodiment, the perfusion characterization data is a function of the MRA image, the quantitative perfusion measurement, and the quantitative relaxation parameter measurement. The perfusion characterization data may be a multi-factor piece of data from which a diagnosis or other observation may be made. The perfusion characterization data produced at 440 improves on conventional systems by considering multiple different data sets associated with simultaneously performed MRAP and MRF.

In one embodiment, the MR apparatus is controlled to simultaneously perform actions 410, 420, and 430 and thus the MR apparatus is controlled to simultaneously acquire the MRA image, the quantitative perfusion measurement, and the quantitative relaxation parameter measurement. In one embodiment, controlling the MR apparatus to simultaneously acquire the MRA image, the quantitative perfusion measurement, and the quantitative relaxation parameter measurement may include controlling the MR apparatus to acquire the MRA image, the quantitative perfusion measurement, and the quantitative relaxation parameter measurement using a single MR pulse sequence.

In one embodiment, controlling the MR apparatus to acquire the quantitative relaxation parameter measurement at 430 includes controlling the MR apparatus to perform MRF. Controlling the MR apparatus to perform MRF may include controlling the MR apparatus to access a set of known signal evolutions, to access an acquired NMR signal, and to compare the signals. The acquired NMR signal is acquired from the volume. Recall that the volume may contain one or more resonant species that simultaneously produce individual NMR signals in response to MRF excitation. The NMR signal may be acquired simultaneously with signals that are used to produce the MRA and the quantitative perfusion measurement.

Controlling the MR apparatus to perform MRF may also include controlling the MR apparatus to find a selected entry in the set of known signals that matches the acquired NMR signal and to identify one or more MR parameters for the volume based on stored MR parameters associated with the selected entry. In one embodiment, the one or more MR parameters include T1 relaxation associated with the resonant species, T2 relaxation associated with the resonant species, off-resonance relaxation associated with the resonant species, and diffusion weighted relaxation associated with the resonant species, T1 being spin-lattice relaxation, T2 being spin-spin relaxation. The quantitative relaxation parameter measurement may then be created from the one or more MR parameters. While T1 and T2 may be used more frequently than other relaxation parameters, in different embodiments the one or more MR parameters may include a diffusion coefficient associated with the volume, a spin density associated with the volume, a proton density associated with the volume, a magnetic field to which the volume was exposed, or a gradient field to which the volume was exposed.

Controlling the MR apparatus to perform MRF may also include controlling the MR apparatus to apply RF energy to the volume in a series of variable sequence blocks, where a sequence block includes one or more excitation phases, one or more readout phases, and one or more waiting phases. The RF energy applied during a sequence block causes the one or more resonant species in the volume to simultaneously produce individual NMR signals. In MRF, at least one member of the series of variable sequence blocks differs from at least one other member of the series of variable sequence blocks in at least N sequence block parameters, N being an integer greater than one. The sequence block parameters may include echo time, flip angle, phase encoding, diffusion encoding, flow encoding, RF pulse amplitude, RF pulse phase, number of RF pulses, type of gradient applied between an excitation portion of a sequence block and a readout portion of a sequence block, number of gradients applied between an excitation portion of a sequence block and a readout portion of a sequence block, type of gradient applied between a readout portion of a sequence block and an excitation portion of a sequence block, number of gradients applied between a readout portion of a sequence block and an excitation portion of a sequence block, type of gradient applied during a readout portion of a sequence block, number of gradients applied during a readout portion of a sequence block, amount of RF spoiling, and amount of gradient spoiling.

Controlling the MR apparatus to perform MRF may also include controlling the MR apparatus to vary the amount of time between sequence blocks in the series of variable sequence blocks, the relative amplitude of RF pulses in sequence blocks in the series of variable sequence blocks, or the relative phase of RF pulses in sequence blocks in the series of variable sequence blocks.

The stored signals and information derived from reference signal evolutions may be associated with a potentially very large data space. The data space for signal evolutions can be partially described by:

$$SE = \sum_{s=1}^{N_S} \sum_{i=1}^{N_A} \sum_{j=1}^{N_{RF}} R_i(\alpha) R_{RF_{ij}}(\alpha, \varphi) R(G) E_i(T1, T2, D) M_0$$

where:
SE is a signal evolution,
$N_S$ is a number of spins,
$N_A$ is a number of sequence blocks,
$N_{RF}$ is a number of RF pulses in a sequence block,
$\alpha$ is a flip angle,
$\Phi$ is a phase angle,
$R_i(\alpha)$ is a rotation due to off resonance,
$R_{RF_{ij}}(\alpha, \Phi)$ is a rotation due to RF differences,
$R(G)$ is a rotation due to a gradient, T1 is spin-lattice relaxation,
T2 is spin-spin relaxation,
D is diffusion relaxation,
$E_i(T1, T2, D)$ is associated with magnetization changes, and
$M_0$ is the default or natural alignment to which spins align when placed in the main magnetic field.

While $E_i(T1,T2,D)$ is provided as an example, in different embodiments, $E_i(T1, T2, D)$ may actually be $E_i(T1, T2, D, \ldots)$, or $E_i(T1, T2 \ldots)$.

Additionally or alternatively, the summation on j could be replaced by a product on j, e.g.:

$$SE = \sum_{s=1}^{N_S} \sum_{i=1}^{N_A} \prod_{j=1}^{N_{RF}} R_i(\alpha) R_{RF_{ij}}(\alpha, \varphi) R(G) E_i(T1, T2, D) M_0$$

In one embodiment, the dictionary may store signals described by:

$$S_i = R_i E_i(S_{i-1})$$

where:
$S_0$ is the default or equilibrium magnetization,
$S_1$ is a vector that represents the different components of magnetization Mx, My, Mz during acquisition block i,
$R_i$ is a combination of rotational effects that occur during acquisition block i, and
$E_i$ is a combination of effects that alter the amount of magnetization in the different states for acquisition block i. In this embodiment, the signal at acquisition block i is a function of the previous signal at acquisition block i-1. Additionally or alternatively, the dictionary may store signals described by:

$$S_i = R_i E_i \sum_{x=1}^{i-1} R_x E_x(S_x)$$

or $$S_i = R_i E_i \prod_{x=1}^{i-1} R_x E_x(S_x)$$

In this embodiment, the signal is a function of the current relaxation and rotation effects and of previous acquisitions. Additionally or alternatively, the dictionary may store signals described by:

$$S_i = \sum_{s=1}^{N_S} R_{s,i} E_{s,i}(S_{s,i-1})$$

In this embodiment, voxels have multiple resonant species or spins, and the effects may be different for every spin within a voxel. Additionally or alternatively, the dictionary may store signals described by:

$$S_i = \sum_{s=1}^{N_S} R_{s,i} E_{s,i} \sum_{x=1}^{i-1} R_{s,x} E_{s,x}(S_{s,x})$$

or $$S_i = \sum_{s=1}^{N_S} R_{s,i} E_{s,i} \prod_{x=1}^{i-1} R_{s,x} E_{s,x}(S_{s,x})$$

In this embodiment, voxels may have multiple resonant species or spins, and the effects may be different for spins within a voxel, and thus the signal may be a function of the effects and the previous acquisition blocks.

While FIG. 4 illustrates various actions occurring in serial, it is to be appreciated that various actions illustrated in FIG. 4 could occur substantially in parallel. By way of illustration, a first process could control MRAP, a second process could control MRF, a third process could produce characterization data, and a fourth process could make a diagnosis based on the characterization data. While four processes are described, it is to be appreciated that a greater and/or lesser number of processes could be employed.

Figure 5:
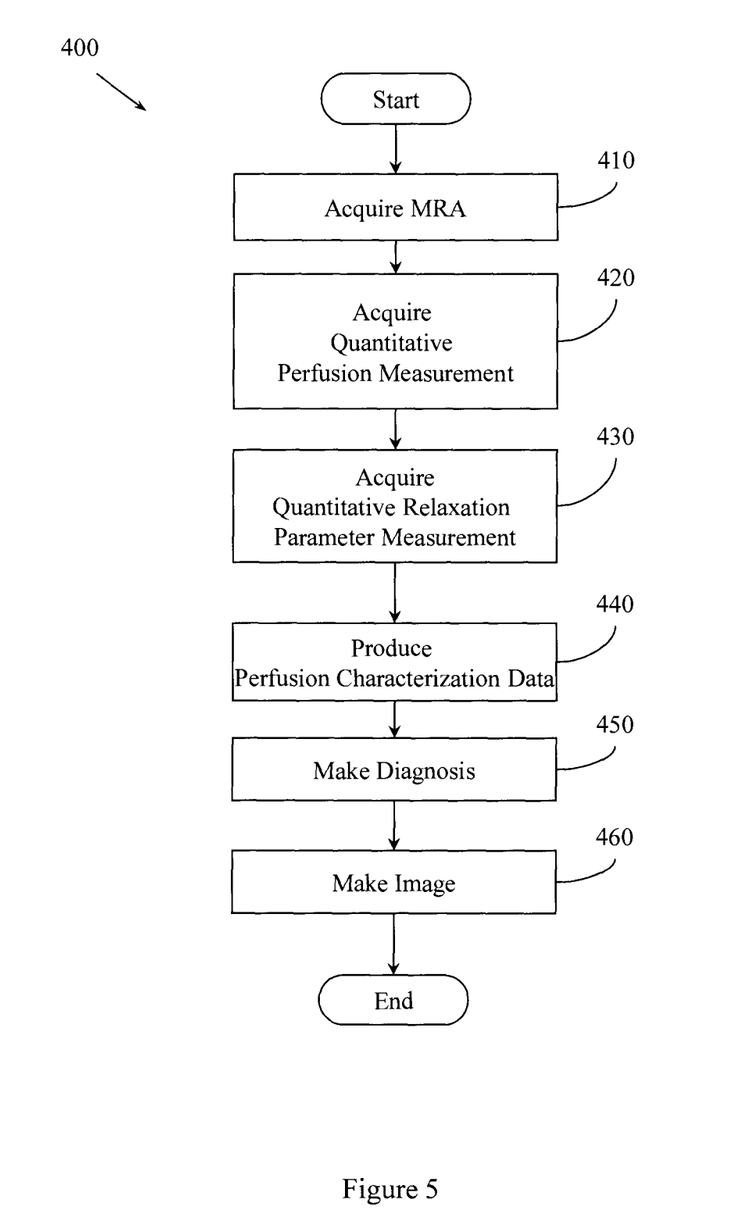
FIG. 5 illustrates an example method associated with simultaneous MRAP with MRF.

FIG. 5 illustrates another embodiment of method 400 (FIG. 4). This embodiment includes actions 410, 420, 430, and 440. However, this embodiment also includes, at 450, making a diagnosis based, at least in part, on the perfusion characterization data. Making a diagnosis at 450 may include diagnosing PAD based, at least in part, on the perfusion characterization data. Recall that the perfusion characterization data is based on multiple data sets and may cover multiple factors. Thus, method 400 improves on conventional systems that consider a single data set or single factor by employing a multi-factor approach that may correspond to multi-factor pathology associated with PAD. In one embodiment, method 400 may make a diagnosis of the severity of PAD.

In different examples, the perfusion characterization data may be used for different purposes. In one example, the perfusion characterization data may provide information from which an efficacy for a treatment for PAD is determined. In another example, the perfusion characterization data provides information concerning vascularization associated with an organ in the volume. For example, vascularization for a liver or kidney may be examined using the combined approach before a transplant or other surgery. Similarly, the perfusion characterization data may provide information concerning vascularization associated with a tumor. Thus, the vascularization associated with a tumor may be examined using the combined approach before a resection, tomosurgery, chemotherapy, or other treatment.

Method 400 may also include, at 460, producing an image. The image may be made from a combination of data associated with the MRA and data acquired from the MRF.

Figure 6:
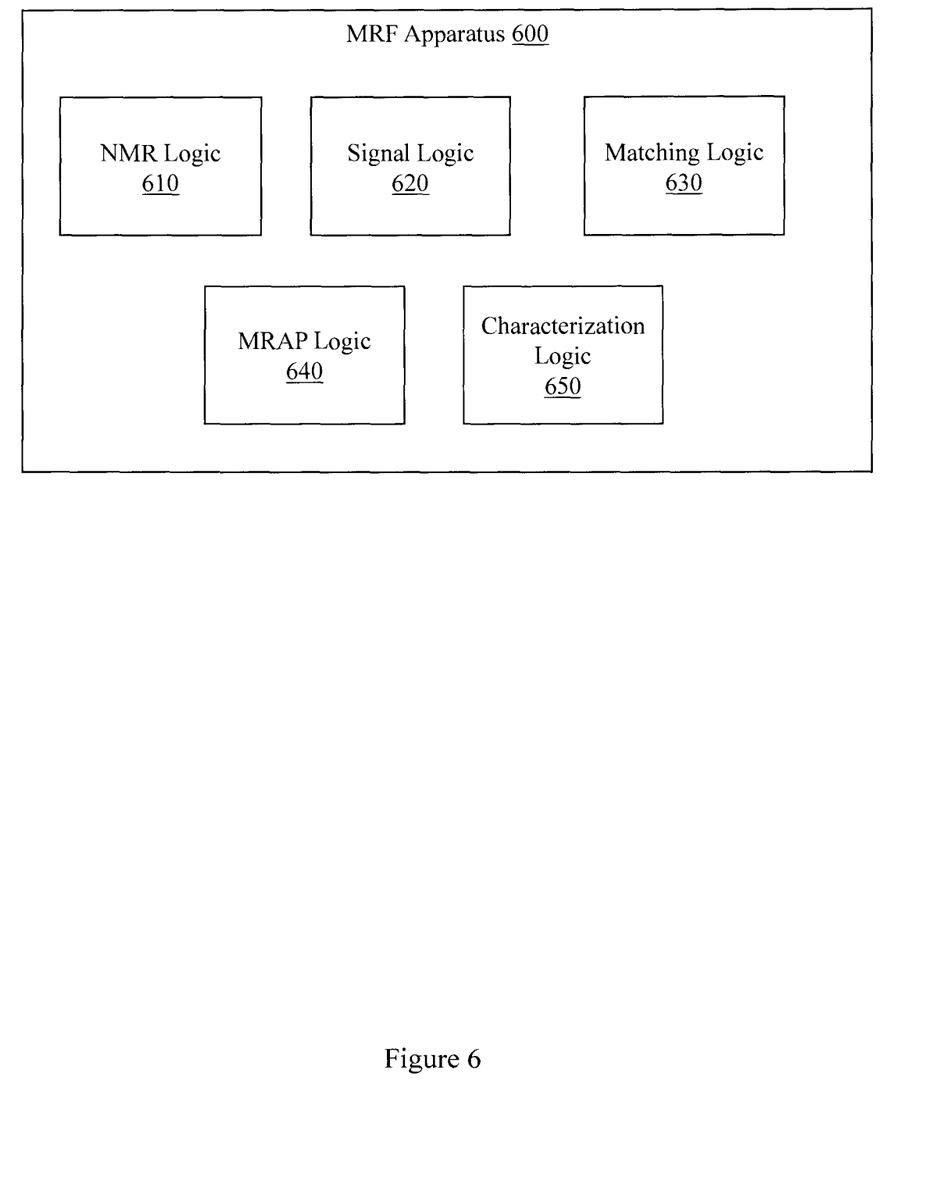
FIG. 6 illustrates an example apparatus associated with simultaneous MRAP with MRF.

FIG. 6 illustrates an MRF apparatus 600. MRF apparatus 600 characterizes an object (e.g., vasculature, lesion, tissue) using data produced simultaneously through magnetic resonance angiography and perfusion (MRAP) and nuclear magnetic resonance fingerprinting (MRF).

MRF apparatus 600 includes an NMR logic 610 that receives a first set of data from an MRF apparatus that repetitively and variably samples a (k, t, E) space associated with an object to acquire a set of NMR signals. The (k, t, E) space is produced as a function of applying RF energy to the object according to an MRF approach. Members of the first set of data are associated with different points in the (k, t, E) space, where t is time and E includes at least one of, T1, T2, and one other parameter, T1 being spin-lattice relaxation, and T2 being spin-spin relaxation. One or more of, t and E, vary non-linearly.

MRF apparatus 600 also includes a signal logic 620. Signal logic 620 produces an NMR signal evolution from the first set of data. MRF apparatus 600 also includes a matching logic 630. Matching logic 630 selects, from a collection of stored signal evolutions, a stored signal evolution that most closely matches the NMR signal evolution.

MRF apparatus 600 also includes an MRAP logic 640. MRAP logic 640 receives a second set of data from the MRF apparatus and produces an MRA and an MRA based perfusion measure for the object from the second set of data. The MRA based perfusion measure may be, for example, $K^{trans}$, which is a function of perfusion (F), density ($\rho$), and hematocrit (Hct) (e.g., $K^{trans}=F \rho (1-Hct)$). In one example, $\rho$ may be assumed to be 1.05 kg/L and Hct may be assumed to be 0.4.

In one embodiment, the first set of data and the second set of data are produced at the same time by a combined MRAP/MRF excitation and acquisition. In one embodiment, the first set of data and the second set of data are produced simultaneously during the same MR acquisition. In one embodiment, there may be some overlap between the first set of data and the second set of data. The first set of data and the second set of data may be produced after the administration of a contrast agent to the object. Apparatus 600 improves over conventional systems by facilitating using a single administration of a contrast agent rather than two administrations.

MRF apparatus 600 also includes a characterization logic 650. Characterization logic 650 characterizes the object based, at least in part, on one or more MR parameters associated with the selected signal evolution, on the MRA, and on the MRA based perfusion measure. The characterization may concern perfusion in a tissue. In one embodiment, the characterization logic 650 provides information concerning T1 associated with the object, T2 associated with the object, a diffusion coefficient associated with the object, a spin density associated with the object, a proton density associated with the object, a magnetic field to which the object was exposed, or a gradient field to which the object was exposed.

In one embodiment, the characterization logic 650 produces a multi-factor MR bio-imaging panel. The multi-factor MR bio-imaging panel may include the MRA based perfusion measure, T1 associated with the object, and T2 associated with the object. While three pieces of information are described being associated with the multi-factor MR bio-imaging panel, a greater or lesser number of different factors may be considered. For example, in one embodiment, the multi-factor MR bio-imaging panel includes the MRA based perfusion measure, T1 associated with the object, T2 associated with the object, and the diffusion co-efficient associated with the object.

Figure 7:
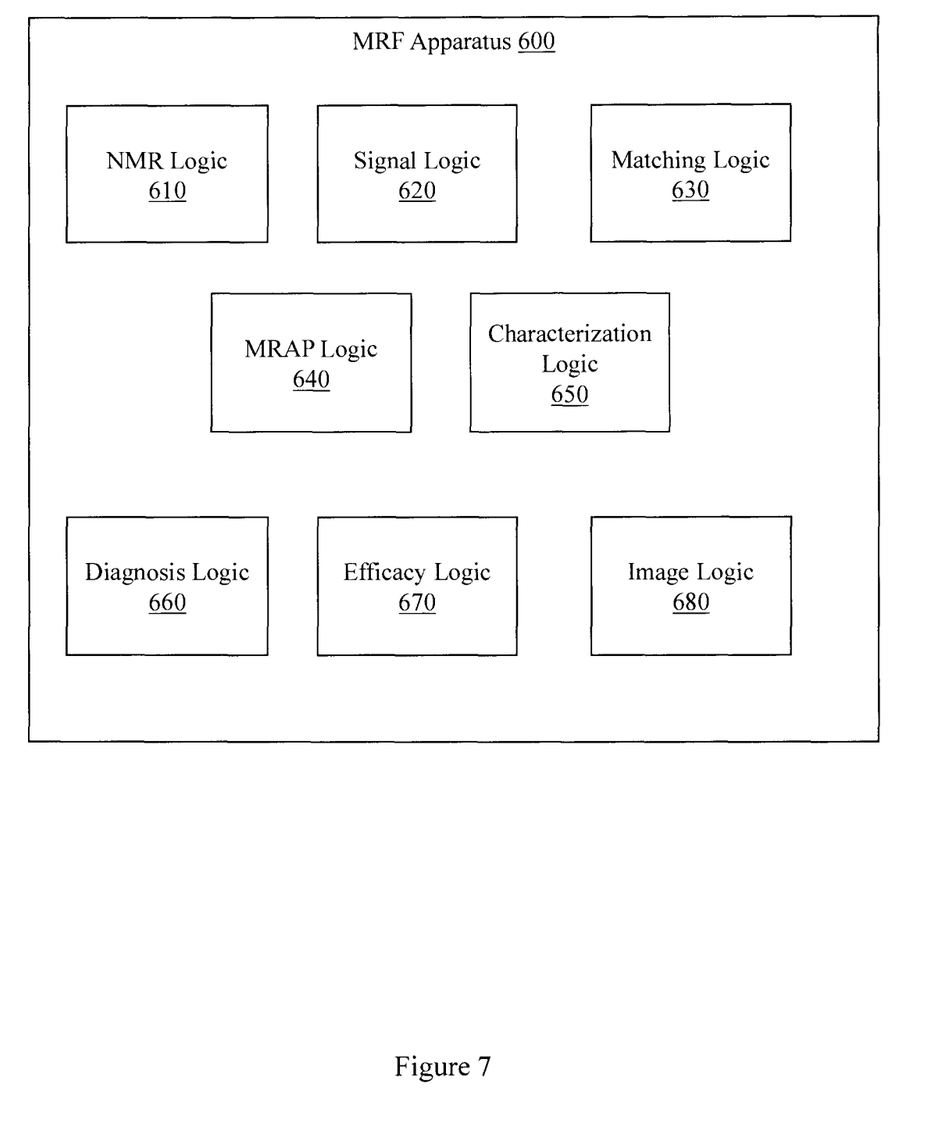
FIG. 7 illustrates an example apparatus associated with simultaneous MRAP with MRF.

FIG. 7 illustrates another embodiment of apparatus 600. This embodiment of apparatus 600 also includes a diagnosis logic 660. Diagnosis logic 660 may diagnose a disease in the object based, at least in part, on the multi-factor MR bio-imaging panel. In one embodiment, the disease is PAD. Additionally, and/or alternatively, the diagnosis logic may diagnose a severity of a disease in the object. The severity diagnosis may be based, at least in part, on the multi-factor MR bio-imaging panel. The diagnosis logic 660 may make the diagnosis based on whether data available in the multi-factor MR bio-imaging panel indicates perfusion above or below a threshold. For example, PAD may be diagnosed for the object when the perfusion for the object as measured by $K^{trans}$ falls below a threshold level.

This embodiment of apparatus 600 also includes an efficacy logic 670. In one embodiment, efficacy logic 670 identifies the efficacy of a treatment to the object based, at least in part, on the multi-factor MR bio-imaging panel. The efficacy may indicate, for example, whether perfusion has been increased, maintained, or decreased in response to a treatment. For treating PAD it may be desirable to attempt to increase perfusion. For treating a tumor, it may be desirable to attempt to reduce perfusion to the tumor.

This embodiment of apparatus 600 includes an image logic 680. In one embodiment, image logic 680 produces an MR image of the object based, at least in part, on the first set of data. For example, a T1 weighted or T2 weighted MR image of the object may be produced from the first data received from the MRF apparatus. In one embodiment, image logic 680 produces an MR image of the object based, at least in part, on the second set of data. For example, an MRA of the object may be produced from the data received from the MRF apparatus. While producing an image from the MRF data or producing an MRA from the MRF data is useful, in one embodiment, image logic 680 may improve over conventional systems by producing an image from both the first set of data and the second set of data. This image may facilitate visually representing information associated with the multi-factor MR bio-imaging panel, which in turn may facilitate making a more accurate diagnosis than is possible with conventional approaches.

Figure 8:
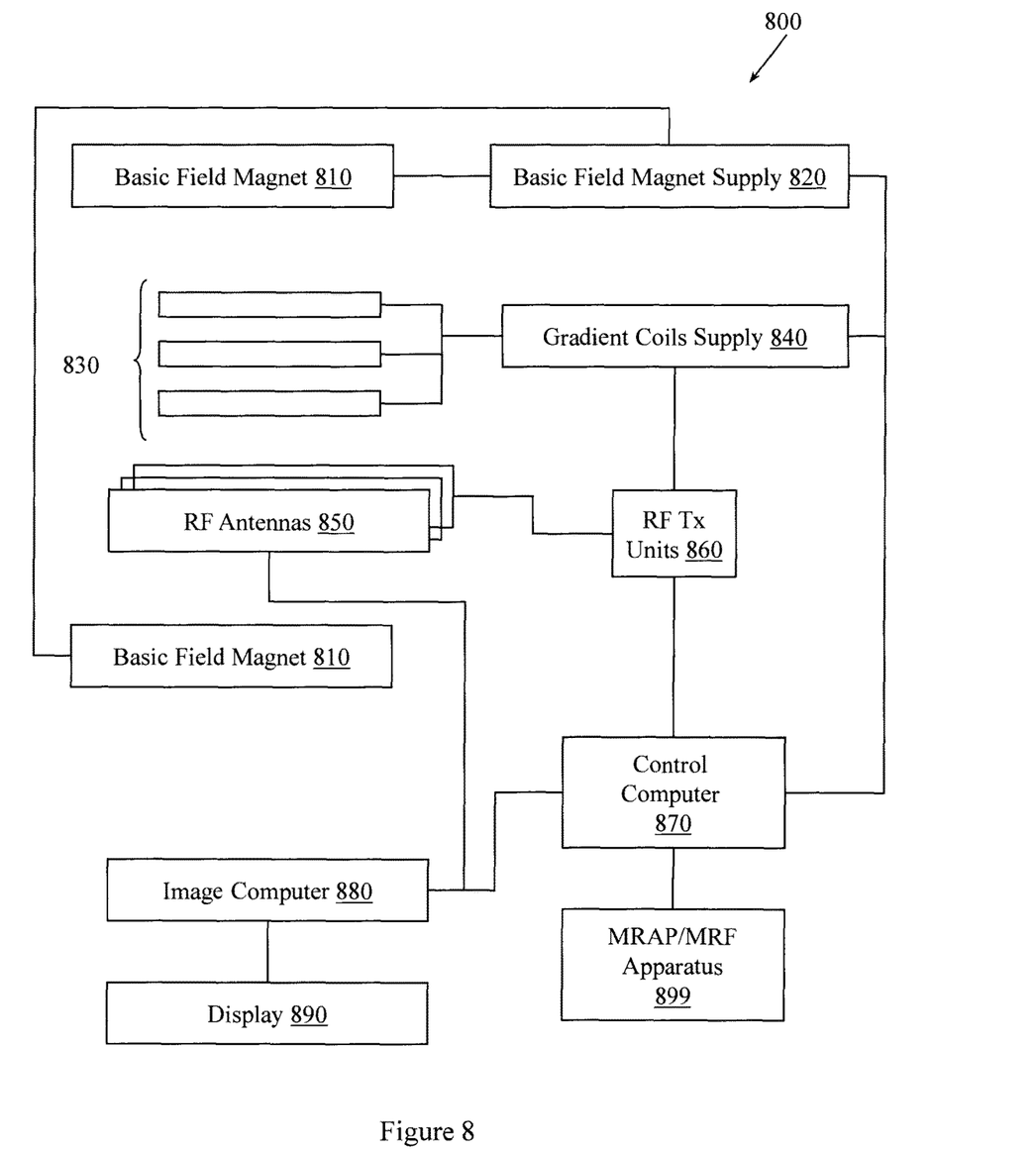
FIG. 8 illustrates an MR apparatus associated with simultaneous MRAP with MRF.

FIG. 8 illustrates an example MR apparatus 800 configured with a combined MRAP and MRF apparatus 899 to facilitate performing MRAP and MR fingerprinting. The apparatus 899 may be configured with elements of example apparatus described herein and/or may perform example methods described herein. While apparatus 899 is illustrated as part of MR apparatus 800, in one example, apparatus 899 may be a separate apparatus or apparatuses.

The apparatus 800 includes a basic field magnet(s) 810 and a basic field magnet supply 820. Ideally, the basic field magnets 810 would produce a uniform $B_0$ field. However, in practice, the $B_0$ field may not be uniform, and may vary over an object being analyzed by the MR apparatus 800. MR apparatus 800 may include gradient coils 830 configured to emit gradient magnetic fields like $G_S$, $G_P$ and $G_R$. The gradient coils 830 may be controlled, at least in part, by a gradient coils supply 840. In some examples, the timing, strength, and orientation of the gradient magnetic fields may be controlled, and thus selectively adapted, during an MR procedure.

MR apparatus 800 may include a set of RF antennas 850 that generate RF pulses and receive resulting nuclear magnetic resonance signals from an object to which the RF pulses are directed. In some examples, how the pulses are generated and how the resulting MR signals are received may be controlled and thus may be selectively adapted during an MR procedure. Separate RF transmission and reception coils can be employed. The RF antennas 850 may be controlled, at least in part, by a set of RF transmission units 860. An RF transmission unit 860 may provide a signal to an RF antenna 850.

The gradient coils supply 840 and the RF transmission units 860 may be controlled, at least in part, by a control computer 870. In one example, the control computer 870 may be programmed to control an NMR device as described herein. Conventionally, the magnetic resonance signals received from the RF antennas 850 can be employed to generate an image and thus may be subject to a transformation process like a two dimensional FFT that generates pixilated image data. The transformation can be performed by an image computer 880 or other similar processing device. The image data may then be shown on a display 890.

However, apparatus 899 facilitates not having to do conventional reconstruction of an image from MR signals received from the RF antennas 850. Thus the RF energy applied to an object by apparatus 800 need not be constrained to produce signals with substantially constant amplitudes or phases. Instead, apparatus 899 facilitates matching received signals to known signals for which a reconstruction, relaxation parameter, or other information is already available.

In one embodiment, apparatus 899 provides means for diagnosing PAD based on a multi-factor panel of indicators corresponding to a multi-factorial model of pathology associated with PAD. The multi-factor panel of indicators may include information from an MRA, MR based perfusion data, and MR based tissue integrity data. Apparatus 899 may produce the multi-factor panel of indicators using a magnetic resonance angiogram, magnetic resonance based perfusion data, and magnetic resonance based tissue integrity data that were acquired simultaneously during a combined MRAP and MRF session. In one embodiment, apparatus 899 may be controlled to perform the combined MRAP and MRF session.

While FIG. 8 illustrates an example MR apparatus 800 that includes various components connected in various ways, it is to be appreciated that other MR apparatus may include other components connected in other ways. In one embodiment, characterizing the object includes providing information concerning items including, but not limited to, T1 associated with the object, T2 associated with the object, a diffusion coefficient associated with the object, a spin density associated with the object, a proton density associated with the object, a magnetic field to which the object was exposed, a gradient field to which the object was exposed, a tissue type of the object, and an identification of the object.

While example systems, methods, and so on have been illustrated by describing examples, and while the examples have been described in considerable detail, it is not the intention of the applicants to restrict or in any way limit the scope of the appended claims to such detail. It is, of course, not possible to describe every conceivable combination of components or methodologies for purposes of describing the systems, methods, and so on described herein. Therefore, the invention is not limited to the specific details, the representative apparatus, and illustrative examples shown and described. Thus, this application is intended to embrace alterations, modifications, and variations that fall within the scope of the appended claims.

To the extent that the term "includes" or "including" is employed in the detailed description or the claims, it is intended to be inclusive in a manner similar to the term "comprising" as that term is interpreted when employed as a transitional word in a claim.

To the extent that the term "or" is employed in the detailed description or claims (e.g., A or B) it is intended to mean "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995).

To the extent that the phrase "one of, A, B, and C" is employed herein, (e.g., a data store configured to store one of, A, B, and C) it is intended to convey the set of possibilities A, B, and C, (e.g., the data store may store only A, only B, or only C). It is not intended to require one of A, one of B, and one of C. When the applicants intend to indicate "at least one of A, at least one of B, and at least one of C", then the phrasing "at least one of A, at least one of B, and at least one of C" will be employed.

To the extent that the phrase "one or more of, A, B, and C" is employed herein, (e.g., a data store configured to store one or more of, A, B, and C) it is intended to convey the set of possibilities A, B, C, AB, AC, BC, ABC, AA . . . A, BB . . . B, CC . . . C, AA . . . ABB . . . B, AA . . . ACC . . . C, BB . . . BCC . . . C, or AA . . . ABB . . . BCC . . . 0 (e.g., the data store may store only A, only B, only C, A&B, A&C, B&C, A&B&C, or other combinations thereof including multiple instances of A, B, or C). It is not intended to require one of A, one of B, and one of C. When the applicants intend to indicate "at least one of A, at least one of B, and at least one of C", then the phrasing "at least one of A, at least one of B, and at least one of C" will be employed.

What is claimed is:

1. An apparatus, comprising:
a nuclear magnetic resonance (NMR) apparatus, comprising a computing device and a display, the computing device including a microprocessor configured to control the NMR apparatus and that is further configured to perform a combined magnetic resonance angiography and perfusion (MRAP)/magnetic resonance fingerprinting (MRF) (MRAP/MRF) excitation to acquire, via the microprocessor configured to perform simultaneous MRAP/MRF acquisition, a first set of data and a second set of data simultaneously,
wherein the first set of data repetitively and variably samples a (k, t, E) space associated with an object to acquire a set of NMR signals, where members of the first set of data are associated with different points in the (k, t, E) space, where k is data acquired by the NMR apparatus, t is time, and E includes at least one of, T1, T2, and one other parameter, T1 being spin-lattice relaxation, and T2 being spin-spin relaxation, and where one or more of, t and E, vary non-linearly, and
wherein the second set of data includes magnetic resonance (MR) angiographic data and perfusion data;
the microprocessor further configured to communicate with the NMR apparatus and is programmed to:
acquire the first set of data and the second set of data, simultaneously, from the object using the MRAP/MRF acquisition;
produce one or more quantitative relaxation parameter, a magnetic resonance angiogram (MRA), and a quantitative perfusion measurement associated with the object, wherein the one or more quantitative relaxation parameter is produced based on the first set of data, and wherein the MRA and the quantitative perfusion measurement are produced based on the second set of data;
produce information concerning vascularization associated with the object based, at least in part, on the one or more quantitative relaxation parameter, the MRA, and the quantitative perfusion measurement; and
display the information concerning vascularization associated with the object on the display.

2. The apparatus of claim 1, controlled by the microprocessor, wherein the NMR apparatus is configured to generate the first data set by applying RF energy to the object in a series of variable sequence blocks to elicit one or more resonant species in the object to simultaneously produce the set of NMR signals, and acquire the set of NMR signals from the object in response to the RF energy to produce the (k, t, E) space.

3. The apparatus of claim 2 further comprising an auto-injector, controlled by the microprocessor, where the first set of data and the second set of data are produced after the auto-injector administers a contrast agent to the object.

4. The apparatus of claim 3, controlled by the microprocessor, where the administration of the contrast agent is a single administration.

5. The apparatus of claim 1, wherein the quantitative relaxation parameter includes a T1 relaxation associated with the object, a T2 relaxation associated with the object, a diffusion coefficient associated with the object, a spin density associated with the object, a proton density associated with the object, a magnetic field to which the object was exposed, or a gradient field to which the object was exposed.

6. The apparatus of claim 1, wherein the object is a patient and wherein the microprocessor is further configured to diagnose a disease, comprising peripheral arterial disease, in the patient based, at least in part, on the one or more quantitative relaxation parameter, the MRA, and the quantitative perfusion measurement.

7. The apparatus of claim 1, wherein the object is a patient and wherein the microprocessor is further configured to diagnose a severity of a disease, comprising peripheral arterial disease, in the patient based, at least in part, on the one or more quantitative relaxation parameter, the MRA, and the quantitative perfusion measurement.

8. The apparatus of claim 1, wherein the microprocessor is further configured to identify the efficacy of a treatment to the object based, at least in part, on the one or more quantitative relaxation parameter, the MRA, and the quantitative perfusion measurement.

9. The apparatus of claim 1, wherein the microprocessor is further configured to produce an MR image of the object based, at least in part, on the first set of data.

10. The apparatus of claim 1, wherein the microprocessor is further configured to produce an MR image of the object based, at least in part, on the second set of data.

11. The apparatus of claim 1, wherein the microprocessor is further configured to produce an MR image of the object based, at least in part, on the first set of data and the second set of data.

12. The apparatus of claim 1, wherein displaying the information concerning vascularization associated with the object further comprises producing an image concerning vascularization associated with the object based, at least in part, on the one or more quantitative relaxation parameter, the MRA, and the quantitative perfusion measurement.

13. The apparatus of claim 1, wherein the information concerning vascularization associated with the object is associated with an organ.

14. The apparatus of claim 1, wherein the information concerning vascularization associated with the object is associated with a tumor.

15. The apparatus of claim 1, wherein the microprocessor is further configured to acquire the first set of data and the second set of data using a single MRAP/MRF acquisition.

* * * * *